(12) United States Patent
Lee et al.

(10) Patent No.: US 9,119,546 B2
(45) Date of Patent: Sep. 1, 2015

(54) R-PEAK DETECTION APPARATUS AND CONTROL METHOD THEREOF

(71) Applicants: Samsung Electronics Co., Ltd., Gyeonggi-do (KR); Industry-Academic Cooperation Foundation Yonsei University, Seoul (KR)

(72) Inventors: Sang-Hun Lee, Gyeonggi-do (KR); Ji-Han Kim, Seoul (KR); Do-Sik Hwang, Seoul (KR); Ung Jang, Seoul (KR)

(73) Assignee: Industry-Academic Cooperation Foundation Yonsei University (KR)

( * ) Notice: Subject to any disclaimer, the term of this patent is extended or adjusted under 35 U.S.C. 154(b) by 0 days.

(21) Appl. No.: 13/723,917

(22) Filed: Dec. 21, 2012

(65) Prior Publication Data

US 2013/0165805 A1 Jun. 27, 2013

(30) Foreign Application Priority Data

Dec. 22, 2011 (KR) .................. 10-2011-0140272

(51) Int. Cl.
*A61B 5/0456* (2006.01)
*A61B 5/04* (2006.01)
*A61B 5/0452* (2006.01)
*A61B 5/00* (2006.01)

(52) U.S. Cl.
CPC .......... *A61B 5/0456* (2013.01); *A61B 5/04012* (2013.01); *A61B 5/04017* (2013.01); *A61B 5/04525* (2013.01); *A61B 5/7203* (2013.01)

(58) Field of Classification Search
CPC .................. A61B 5/04525; A61B 5/0456
USPC ....................................... 600/521
See application file for complete search history.

(56) References Cited

U.S. PATENT DOCUMENTS 4,893,632 A * 1/1990 Armington .................. 600/509
2010/0113953 A1 * 5/2010 Marcovecchio et al. ..... 600/515

* cited by examiner

*Primary Examiner* — Michael Kahelin
(74) *Attorney, Agent, or Firm* — The Farrell Law Firm, P.C.

(57) ABSTRACT

A method of controlling of an R-peak detection apparatus, which detects an R-peak from an ElectroCardioGram (ECG) signal, includes receiving the ECG signal, reading out a pre-stored ECG template, comparing the EG signal with the pre-stored ECG template to determine a similarity between the ECG signal and the pre-stored ECG template and determining whether the similarity is equal to or greater than a threshold value, and determining a corresponding interval as the R-peak when the similarity is equal to or greater than the threshold value.

18 Claims, 11 Drawing Sheets

R-PEAK DETECTION APPARATUS AND CONTROL METHOD THEREOF

PRIORITY

This application claims priority under 35 U.S.C. §119(a) to Korean Application Serial No. 10-2011-0140272, which was filed in the Korean Intellectual Property Office on Dec. 22, 2011, the contents of which are incorporated herein by reference.

BACKGROUND OF THE INVENTION

1. Field of the Invention

The present invention relates generally to an apparatus and control method for detecting an R-peak from an ElectroCardioGram (ECG), which is an electric signal output from the heart of a living body.

2. Description of the Related Art

A medical-electric convergence technique for electrically interpreting a health-related symptom from a living body has recently been developed in light of the increased interest in physical health. Particularly, since an intake of food with high fat or cholesterol content has increased, heart-related disease has rapidly increased. Thus, development of a technique for continually monitoring an abnormal symptom of cardio motility has become a priority.

Accordingly, a process for electrically interpreting an ECG output from a user has been developed. Detecting an R-peak interval included in the ECG is a required aspect of the ECG interpretation process.

Detecting an R-peak included in the ECG in the conventional art is largely divided into a method of using a differentiation and a method of using a wavelet. The method of using the differentiation employs a method of performing a differential operation on an input ECG signal and then applying an appropriate threshold value to a differential coefficient that is obtained by performing the differential operation, thereby detecting the R-peak. The R-peak has a steep gradient relative to time, compared with other intervals of the ECG signal, and accordingly, an interval having a gradient, i.e., a differential coefficient equal to or greater than a set level, is determined as the R-peak.

The method of using the wavelet involves performing wavelet transformation on the input ECG signal to use a modulus maxima line in a wavelet domain.

However, the conventional R-peak detection methods, including the two described above, have problem in that an input signal is greatly affect by noise and it is highly probable that an intense T-peak will be mistaken as the R-peak. Accordingly, there is a need in the art for the development of an R-peak detection technique that is robust against signal noise and the intense T-peak.

SUMMARY OF THE INVENTION

Accordingly, the present invention has been made to solve the above-described problems described above and to respond to the above-described demand.

An aspect of the present invention is to provide an apparatus and a method for R-peak detection by using an ECG template.

In accordance with an aspect of the present invention, a method of controlling of an R-peak detection apparatus which detects an R-peak from an ECG signal includes receiving the ECG signal, reading out a pre-stored ECG template, comparing the ECG signal with the ECG template to determine a similarity between the ECG signal and the ECG template and determining whether the similarity is equal to or greater than a threshold value, and determining a corresponding interval as the R-peak when the similarity is equal to or greater than the threshold value.

In accordance with another aspect of the present invention, an R-peak detection apparatus for detecting an R-peak from an ECG signal includes a sensor unit which senses the ECG signal, a storage unit which stores the ECG template, and a controller which compares the ECG signal with the ECG template to determine a similarity between the ECG signal and the ECG template, determines whether the similarity is equal to or greater than a threshold value, and determines a corresponding interval as the R-peak when the similarity is equal to or greater than the threshold value.

BRIEF DESCRIPTION OF THE DRAWINGS

The above and other aspects, features, and advantages of the present invention will be more apparent from the following detailed description taken in conjunction with the accompanying drawings, in which.

DETAILED DESCRIPTION OF EMBODIMENTS OF THE PRESENT INVENTION

Figure 1:
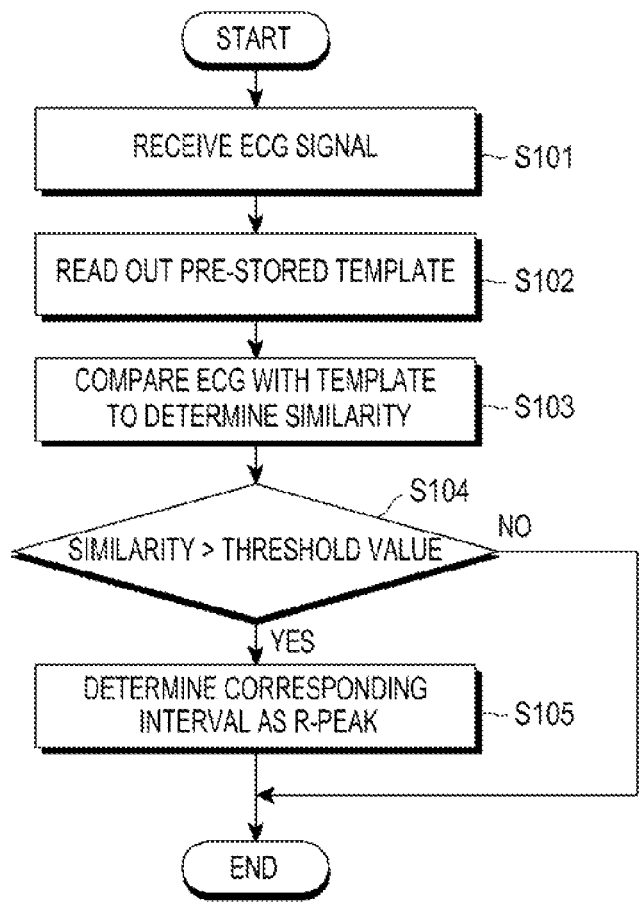
FIG. 1 illustrates a control method of an R-peak detection apparatus according to an embodiment of the present invention.

Hereinafter, embodiments of the present invention will be described with reference to the accompanying drawings. In the following description, identical elements will be designated by identical reference numerals throughout the drawings. Further, in the following description of the present invention, a detailed description of associated known functions or elements will be omitted for the sake of clarity and conciseness.

FIG. 1 illustrates a control method of an R-peak detection apparatus according to an embodiment of the present invention.

The R-peak detection apparatus receives an ECG signal from a user (S101).

The R-peak detection apparatus includes a sensing means for sensing the ECG signal. For example, the sensing means includes at least one electrode, which can be attached to the user, i.e., a living body. The electrode may be silver; however, it will be easily understood by those skilled in the art that the sensing means is not limited as long as the sensing means is capable of detecting the ECG signal from the living body. The R-peak detection apparatus senses at least one living body signal from the at least one electrode and receives the ECG signal based on the sensed at least one signal.

Also, the R-peak detection apparatus may be configured independently of the sensing means to receive the ECG signal from the independent sensing means. In this case, the R-peak detection apparatus includes an interface that can receive a specific electric signal from the sensing means.

The R-peak detection apparatus reads out a pre-stored ECG template for comparison with the ECG signal input by the above-described configuration (S102). The ECG template may be an object to be compared with an input raw data in order to detect a specific section of the ECG signal. The ECG template may be an ECG signal model obtained in an environment in which noise is minimized and may be a signal model in which noise removal and error correction are performed with respect to the obtained ECG signal model. The ECG template may be a learned ECG signal model that is generated based on repeated performance of comparison between the ECG signal and the ECG template, which will be described below.

The R-peak detection apparatus compares the obtained ECG template with the ECG signal to determine a similarity between both signals (S103). The similarity indicates a similarity between waveforms of the ECG template and the ECG signal.

Figure 2:
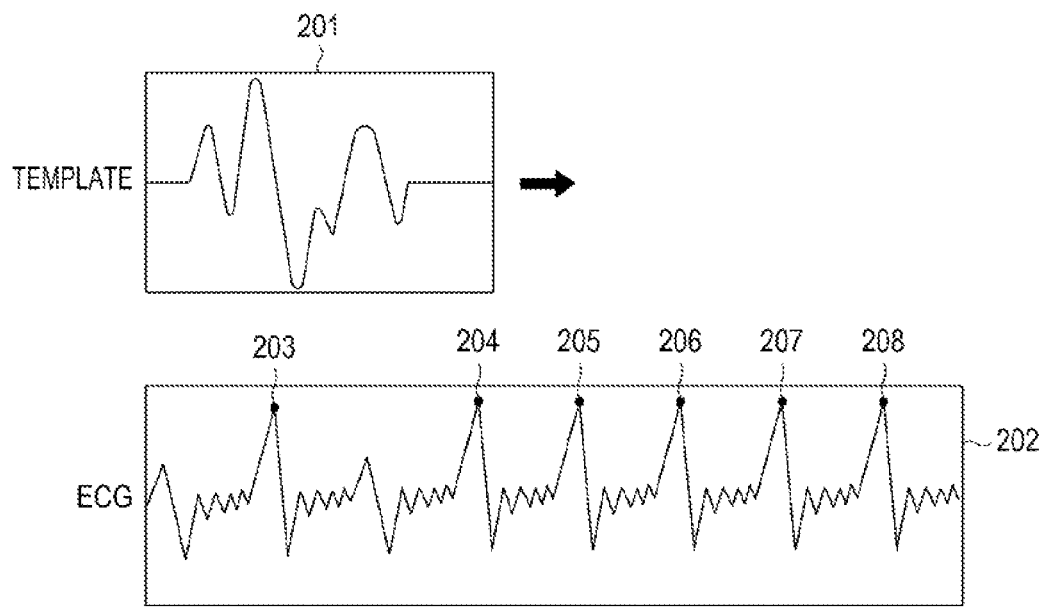
FIG. 2 illustrates a process of determining a similarity based on a correlation according to an embodiment of the present invention.

The R-peak detection apparatus according to an embodiment of the present invention determines a similarity based on a correlation of the ECG template and the ECG signal. FIG. 2 illustrates a method of determining a similarity based on a correlation according to an embodiment of the present invention.

As illustrated in FIG. 2, the R-peak detection apparatus performs a correlation computation process while moving the ECG template 201 in a time direction with respect to the input ECG signal 202 to determine a correlation between two signals. The R-peak detection apparatus samples the input ECG signal in an analog form in a preset interval and then quantizes the ECG signal to extract time serial data of the ECG signal. The time serial data of the ECG signal is assumed to be, for example, [x1, x2, . . . , xn].

Here, x denotes the ECG signal and a number subscript n denotes an n-th data. The R-peak detection apparatus repeats the same step with respect to the ECG template to set time serial data of the ECG template, which is assumed to be [y1, y2, . . . , yn] where y denotes a data of the ECG template, and a number subscript n denotes an n-th data.

The R-peak detection apparatus stores the ECG template in a form of a sampled time serial data, or the R-peak detection apparatus stores the ECG template in analog form and then generates time serial data sampled in an appropriate period based on a form of the input ECG signal. The R-peak detection apparatus determines a correlation $r_{xy}$ by using the time serial data [x1, x2, . . . , xn] of the ECG signal, the time serial data [y1, y2, . . . , yn] of the ECG template, and Equation (1) as follows.

$$r_{xy} = \frac{\sum_{i=1}^{n}(x_i - \bar{x})(y_i - \bar{y})}{\sqrt{\sum_{i=1}^{n}(x_i - \bar{x})^2}\sqrt{\sum_{i=1}^{n}(y_i - \bar{y})^2}} \qquad (1)$$

In Equation (1), $\bar{x}$ denotes an average of the time serial data of the ECG signal and $\bar{y}$ denotes an average of the time serial data of the ECG template. Further, the above subscript i denotes an i-th time serial data, and n denotes a total number of pieces of the time serial data.

A resulting value of the correlation value $r_{xy}$ according to Equation (1) has a value that approximates 1 as the similarity between the ECG signal and the ECG template is greater and which approximates 0 as the similarity is smaller.

An interval in which a value of the similarity is greater may be estimated as the R-peak based on a general characteristic of the ECG signal. The estimation is based on an interval in which the similarity between a form of the template and the R-peak of the input ECG signal is greater than that in the other intervals.

The R-peak detection apparatus determines whether a magnitude of similarity such as, for example, the correlation determined by Equation (1) is greater than a threshold value (step S104). The threshold value may be statistically determined, and the R-peak detection apparatus may determine an interval in which the similarity is equal to or greater than 0.8 as the R-peak (S105). The threshold value may be determined statistically and may be updated in connection with an update of the template by a repeated process, which will be described in further detail later.

As described above, the R-peak detection apparatus detects the R-peak by comparing the ECG signal with the pre-stored ECG template, unlike the prior art in which the ECG signal itself is interpreted. Accordingly, the R-peak detection apparatus minimizes an influence of noise that can be generated by interpreting the ECG signal itself and an influence of an intense T-peak.

Figure 3:
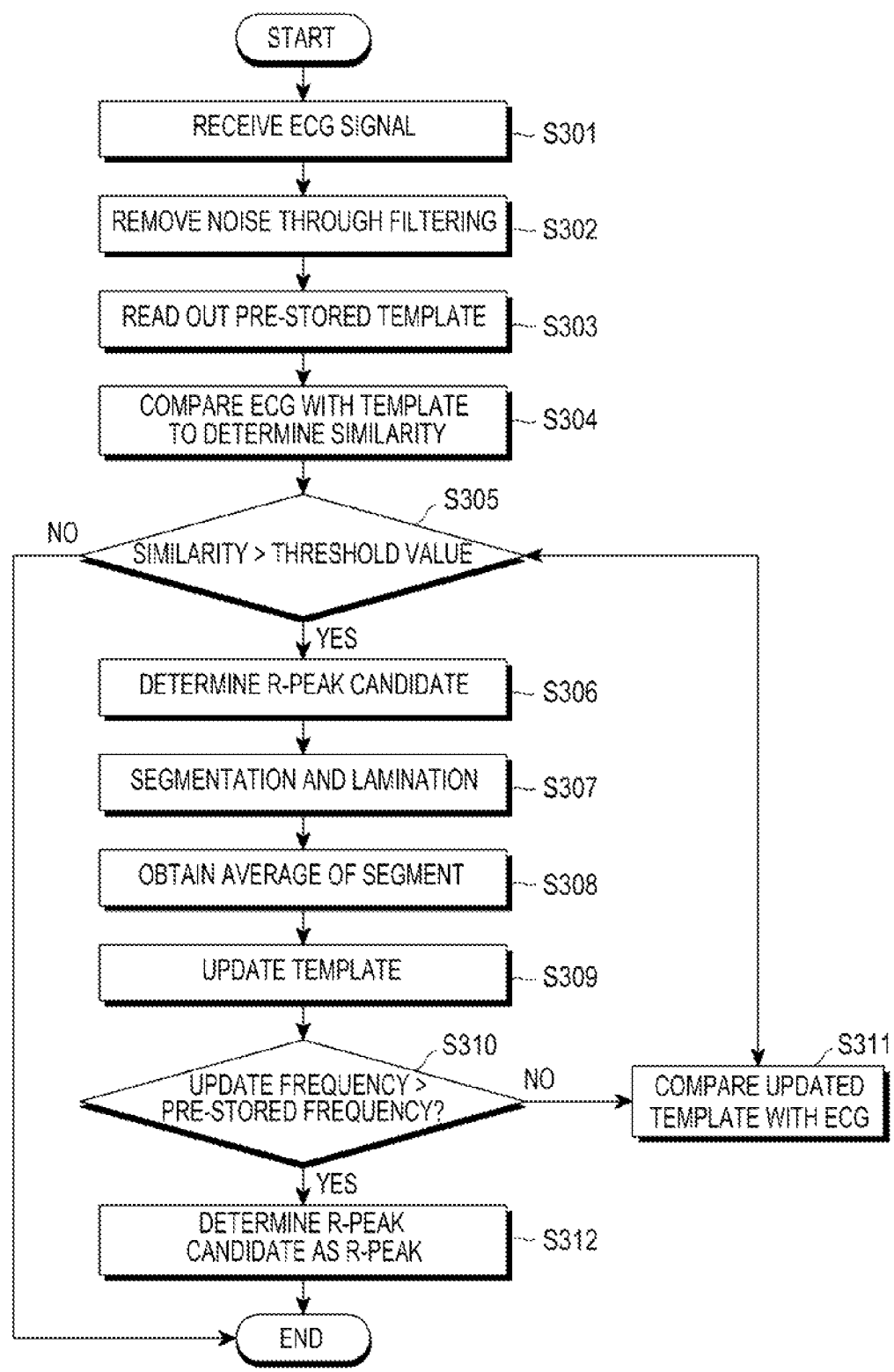
FIG. 3 illustrates a control method of an R-peak detection apparatus according to another embodiment of the present invention.

FIG. 3 illustrates a control method of an R-peak detection apparatus according to another embodiment of the present invention.

The R-peak detection apparatus receives the ECG signal (S301).

The R-peak detection apparatus removes noise by performing filtering with respect to the input ECG signal (S302). The R-peak detection apparatus includes at least one of a high pass filter, a low pass filter, and a band pass filter, and thus blocks a frequency band having much noise.

The R-peak detection apparatus reads out the pre-stored ECG template (S303).

The R-peak detection apparatus compares the ECG signal with the read out ECG template to determine the similarity (S304).

The R-peak detection apparatus determines whether the determined similarity is greater than the threshold value (S305) and determines an interval of the ECS signal in which the similarity is greater than the threshold value as an R-peak candidate.

The R-peak detection apparatus performs segmentation on the ECG signal with respect to the R-peak candidate (S307). In other words, the R-peak candidate appears in the ECG signal to be repeated to in an interval, and the R-peak detection apparatus generates a plurality of ECG signal segments that have identical interval lengths, by segmenting the ECG signal at every interval.

The R-peak detection apparatus laminates the generated plurality of the ECG signal segments. In other words, the R-peak detection apparatus arranges the ECG signal segments together on one plane. The R-peak detection apparatus averages the plurality of the ECG signals laminated together on one plane (S308). For example, the R-peak detection apparatus generates each time serial data with respect to the plurality of the ECG signal segments and obtains average values corresponding to respective time intervals.

The R-peak detection apparatus updates an averaged graph or time serial data of the plurality of the ECG signal segments in a new ECG template (S309).

The R-peak detection apparatus performs a step related to the above-described update of the ECG template by a preset number of times (i.e., frequency), and it is determined whether the update frequency is greater than the pre-stored frequency (S310). When the R-peak detection apparatus performs the updating process of the ECG template by the preset number of times or less ('No' to S310), the R-peak detection apparatus compares the updated ECG template with the ECG signal input in S301 or the ECG signal filtered in S302 (S311).

The R-peak detection apparatus repeats steps S305 through S309 by using the updated ECG template. In other words, the R-peak detection apparatus compares the updated ECG template and the ECG signal to determine an interval in which the similarity is equal to or greater than the threshold value as the R-peak candidate, and performs segmentation on the ECG signal based on the updated R-peak candidate. The generated plurality of the ECG signal segments may be averaged after lamination to again update a new ECG template.

When the R-peak detection apparatus performs the updating of the ECG template over the preset number of times ('Yes' to S311), the R-peak detection apparatus determines the R-peak candidate as the R-peak (S312).

The threshold in step S305 may be determined differently according to a number of updates of the ECG template performed. More specifically, the threshold may be determined according to Equation (2) as follows.

$$Th(k)=M(k)+\alpha V(k) \quad (2)$$

In Equation (2), k is a number of the updates of the ECG template performed, Th(k) denotes the threshold value, M(k) and V(k) respectively denote an average and a distribution of the correlation between the ECG signal and the ECG template. Also, α may be a weight of the distribution and may be, for example, 20. As described above, the R-peak detection apparatus according to an embodiment of the present invention obtains the ECG template, which is more substantially similar to an actual ECG signal by updating the ECG template, and obtains the ECG template that is different for each user. A different threshold based on Equation (2) may be applied to each update of the ECG template and an effect of detecting an R-peak that is more robust against noise may be created.

Figure 4:
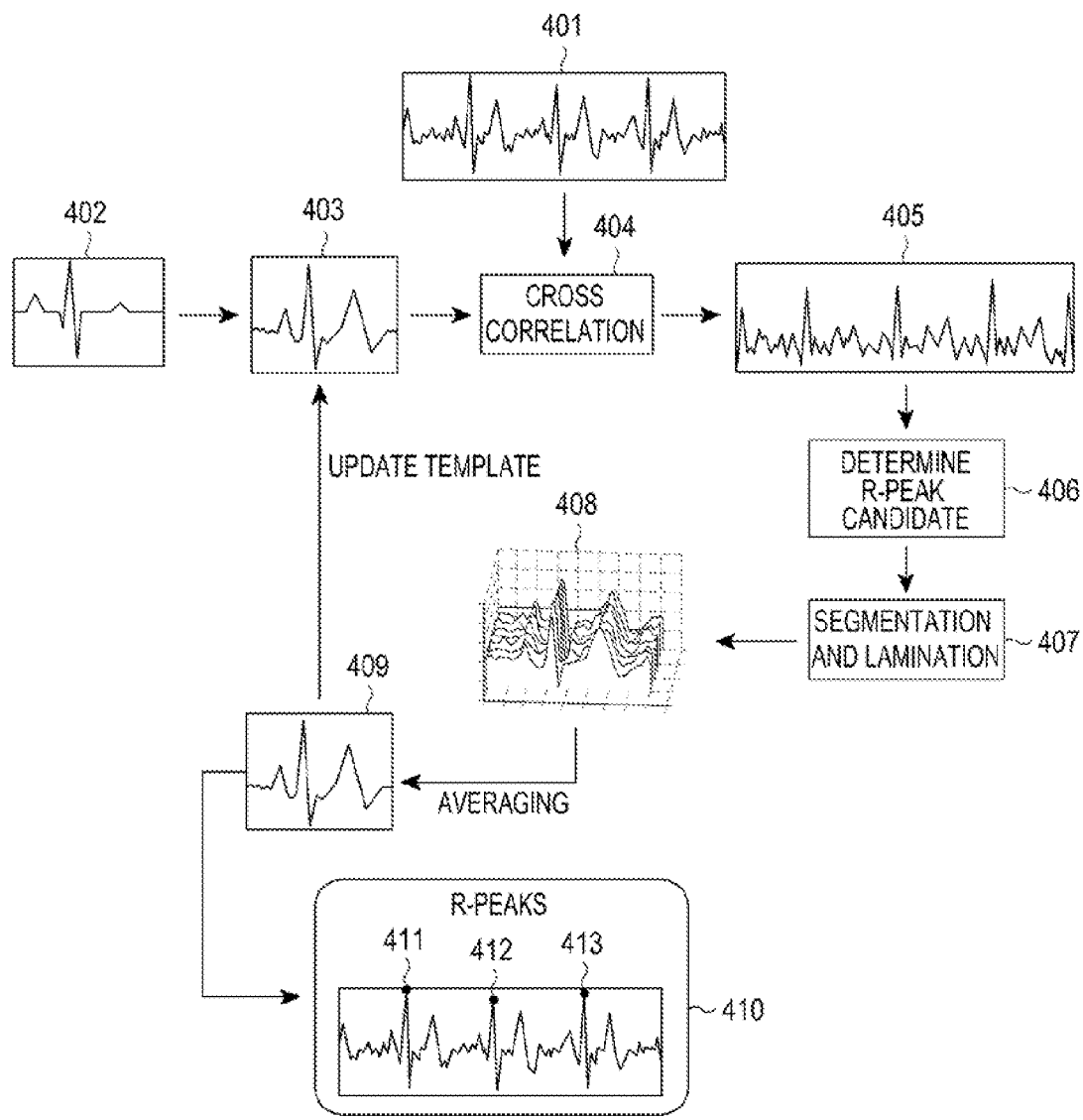
FIG. 4 illustrates a process of updating an ECG template according to an embodiment of the present invention.

FIG. 4 illustrates a process of updating an ECG template according to an embodiment of the present invention.

As illustrated in FIG. 4, the R-peak detection apparatus receives raw data of an ECG signal or an ECG signal 401 on which pre-treatment such as filtering is performed. It can be seen that the ECG signal 401 has a plurality of sections that are estimated as the R-peak. An x-axis of the ECG signal 401 represents time and a y-axis represents a voltage value. The ECG signal 401 is illustrated in analog signal form; however, the ECG signal 401 may be time serial data that is sampled in an interval and quantized, as described above.

The R-peak detection apparatus reads out the ECG template 402, which is identified by an identification number 402 and may be an initial ECG template that is not updated. The ECG template 403 identified by an identification number 403 may be the updated ECG template. In an initial comparison, the ECG template 402 and the ECG template 403 may be identical.

The R-peak detection apparatus compares the ECG signal 401 and the ECG template and determines, for example, the correlation based on Equation (1) (404). An identification number 405 denotes a correlation according to an embodiment of the present invention. In 405, the x-axis represents time and the y-axis represents a correlation value.

The R-peak detection apparatus determines an interval in which the correlation is equal to or greater than the threshold determined by Equation (2) (406) and performs segmentation and lamination based on the R-peak candidate (407).

A graph 408 shows a plurality of ECG signal segments laminated together on one plane. The R-peak detection apparatus averages the plurality of the ECG signal segments to generate an averaged graph of R-peaks 409.

The R-peak detection apparatus updates the averaged graph 409 in the new ECG template and repeats the above-described updating process by the preset number of times.

After repeating the updating process by the preset number of times, the R-peak detection apparatus determines the R-peak candidates 411, 412, 413 that are updated in an updated correlation graph 410 as the R-peak.

FIGS. 5A through 5F illustrate a process of updating an ECG template and a process of repeating an update, according to the present invention.

Figure 5A:
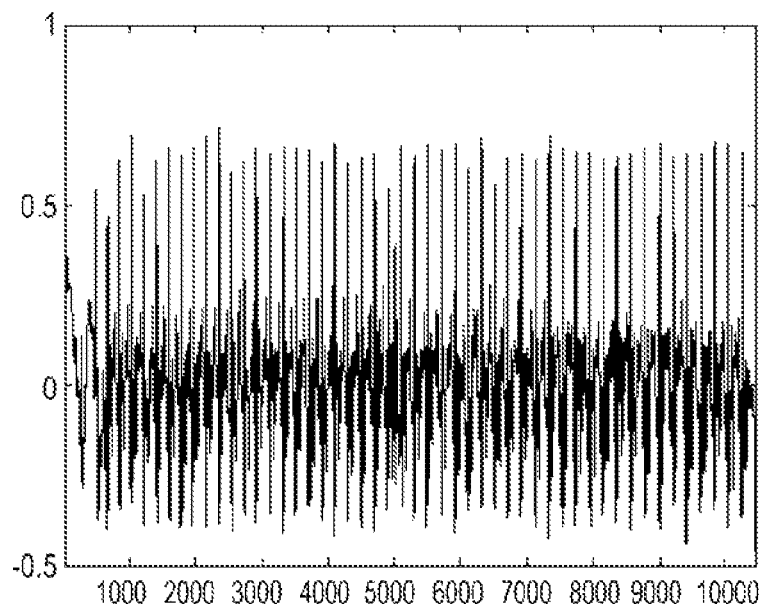
FIGS. 5A through 5F illustrate a process of updating an ECG template and a process of repeating an update.
Figure 5B:
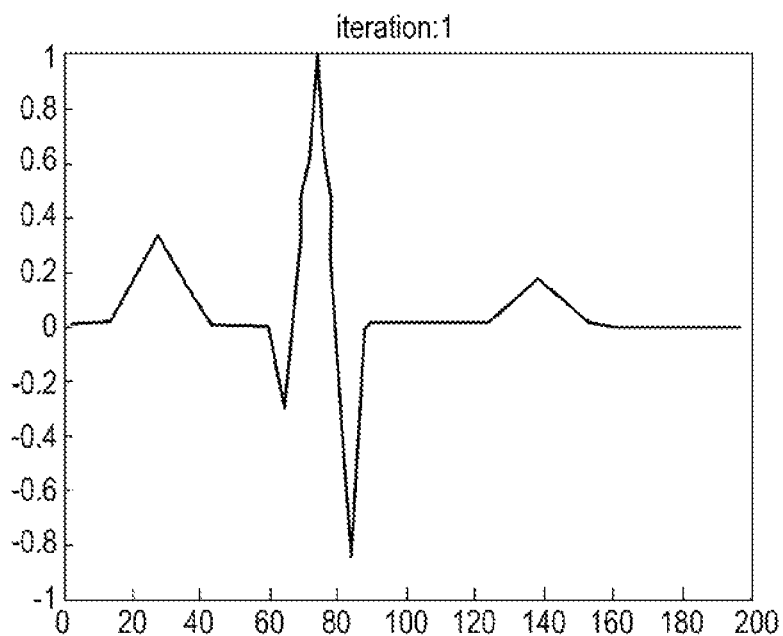
Figure 5C:
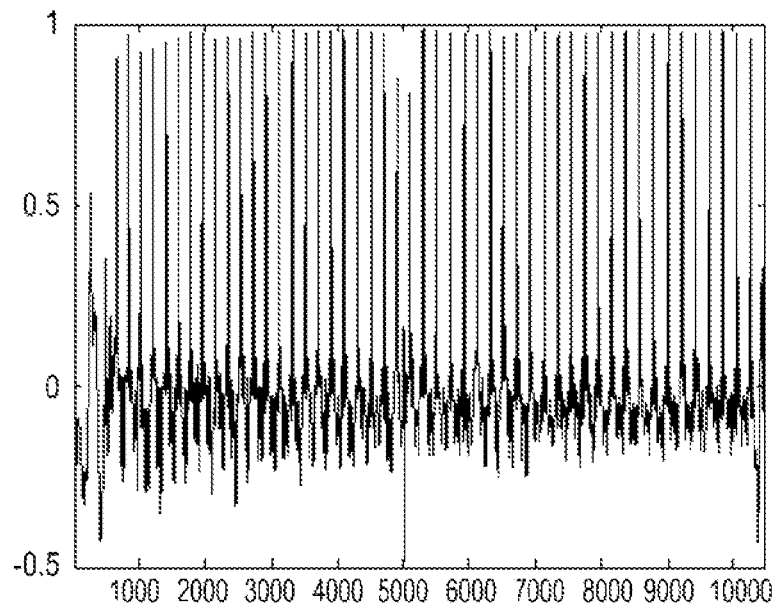
Figure 5D:
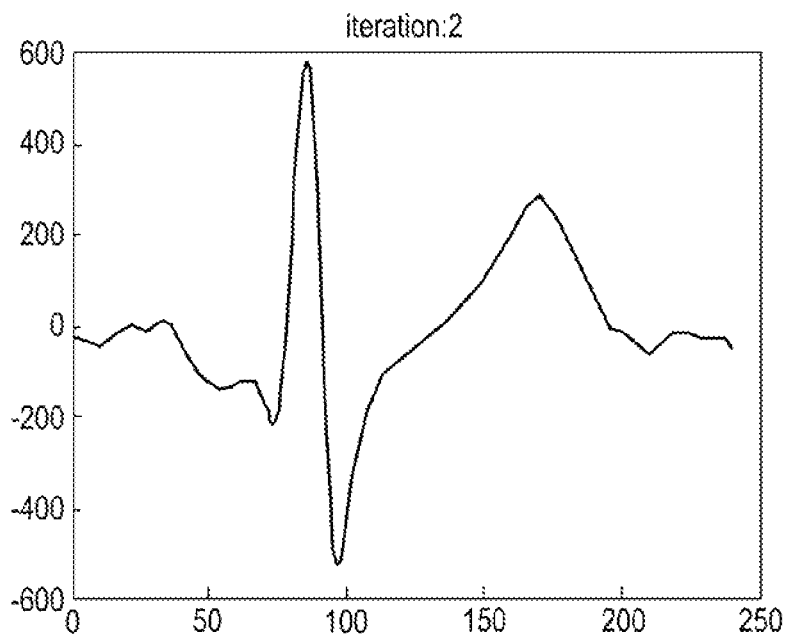
Figure 5E:
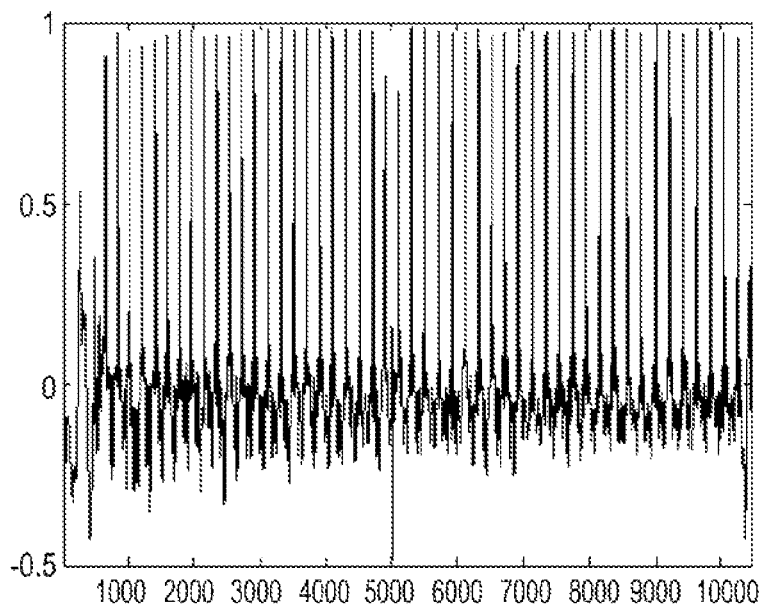
Figure 5F:
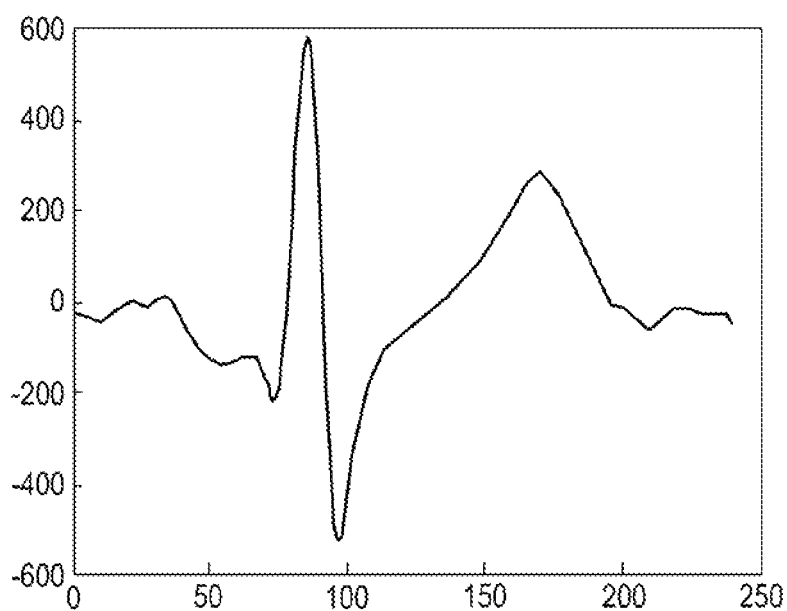

FIG. 5A is a correlation graph in a first repeated process, and FIG. 5B is an ECG template corresponding thereto (i.e., to the first repeated process). FIG. 5C is a correlation graph in a second repeated process, FIG. 5D is an ECG template corresponding thereto, FIG. 5E is a correlation graphs in a third repeated process, and FIG. 5F is an ECG template corresponding thereto. It can be seen that the form of the ECG template becomes more similar to the actual ECG signal as the update of the ECG template proceeds from FIG. 5B to FIG. 5D and FIG. 5F.

Figure 6A:
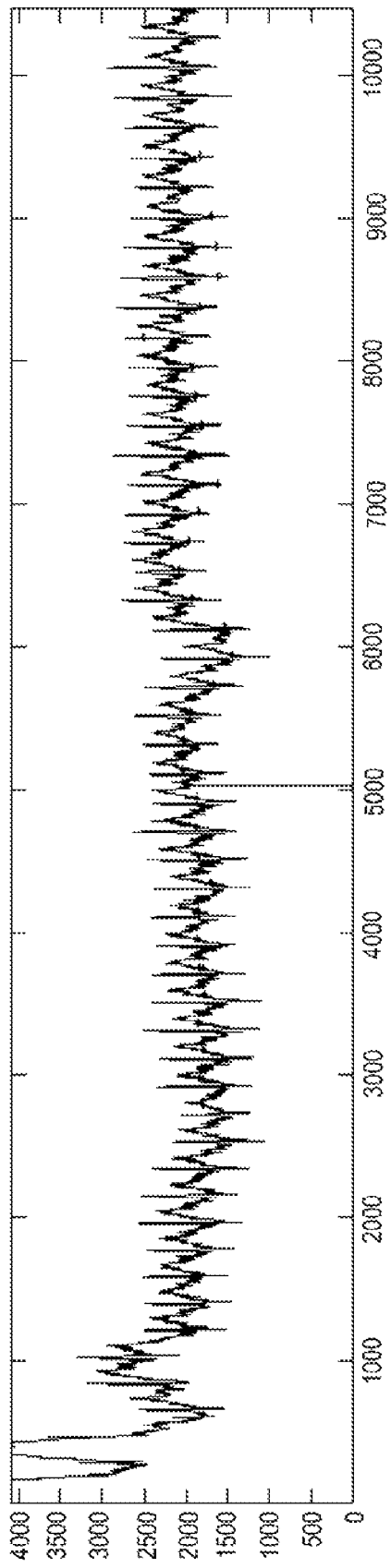
FIGS. 6A and 6B respectively illustrate an R-peak detected by a conventional R-peak detection apparatus and an R-peak detected by an R-peak detection apparatus according to an embodiment of the present invention.
Figure 6B:
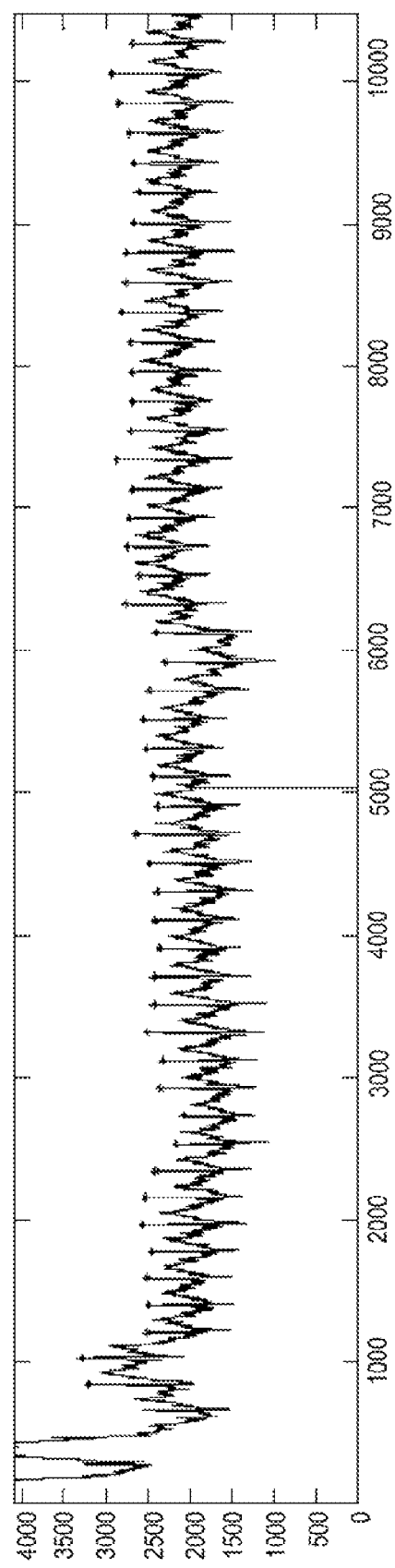

FIGS. 6A and 6B respectively illustrate an R-peak detected by a conventional R-peak detection apparatus and an R-peak detected by an R-peak detection apparatus according to an embodiment of the present invention.

As illustrated in FIG. 6A, the R-peak detected by the conventional R-peak detection apparatus includes noise; however, as illustrated by "+" in FIG. 6B, it can be seen that the R-peak may be detected without an influence of the noise.

Figure 7A:
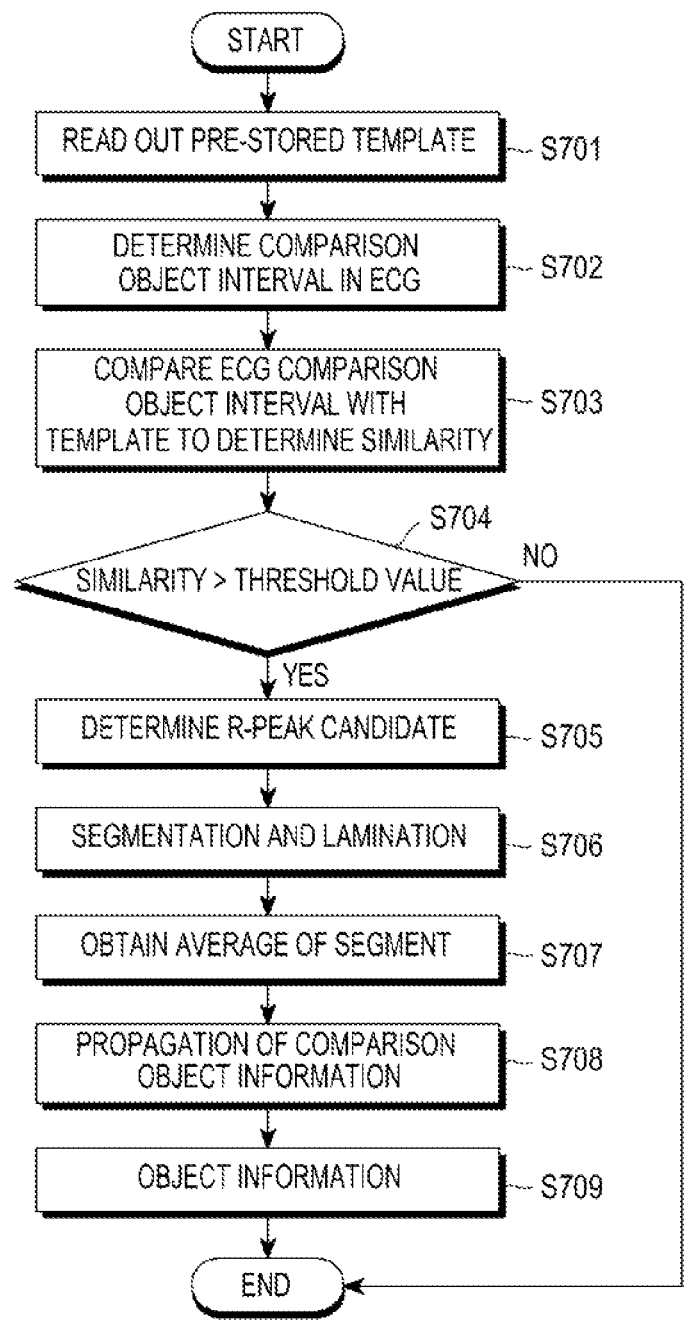
FIG. 7A illustrates a process of updating an ECG template according to another embodiment of the present invention.

FIG. 7A illustrates a process of updating an ECG template according to another embodiment of the present invention. A process of detecting the R-peak other than a process of updating the ECG template of FIG. 7 is the same as described above in FIG. 1 or FIG. 3, and thus, a description thereof will be omitted.

Figure 7B:
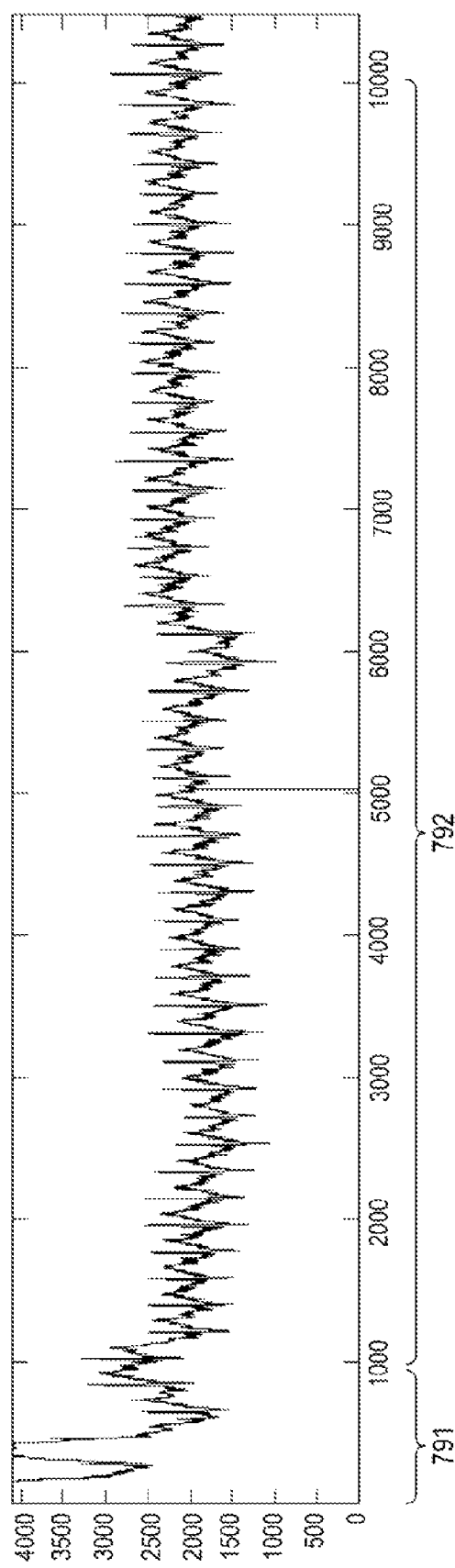
FIG. 7B illustrates a comparison object interval according to an embodiment of the present invention.

The R-peak detection apparatus reads out the pre-stored template (S701). The R-peak detection apparatus determines, from the ECG signal, a comparison object interval to be compared with the ECG template (S702). The R-peak detection apparatus determines, for example, an initial part interval of the ECG signal as the comparison object interval. FIG. 7B illustrates the determination of a comparison object interval according to an embodiment of the present invention, and for example, the R-peak detection apparatus determines an initial part interval 791 of the ECG signal as the comparison object interval. The comparison object interval 791 may be, for example, initial 2 or 3 periods.

Referring back to FIG. 7A, the R-peak detection apparatus compares the comparison object interval of the ECG signal with the ECG template to determine the similarity (S703). The similarity between the comparison object interval and the ECG template may be, for example, the correlation.

The R-peak detection apparatus determines whether the determined similarity is greater than the threshold value (S704) and determines an interval in which the similarity is greater than the threshold value ('Yes' to S704) as the R-peak candidate (S705). The R-peak detection apparatus performs segmentation and segment lamination based on the R-peak candidate (S706) and updates a template for a comparison object interval 791 by calculating an average segment (S707).

The R-peak detection apparatus repeats updating the template with respect to the comparison object interval 791 and confirms the ECG template after performing the update by a preset number of times.

When performing a comparison with the ECG signal by using the confirmed ECG template, the ECG template is propagated with respect to remaining intervals (792 of FIG. 7B) of the ECG signal (S709).

As in the above-described configuration, by performing the update of the ECG template with respect to only a partial interval of the ECG signal, a computation amount and a computation time are effectively reduced.

Figure 8:
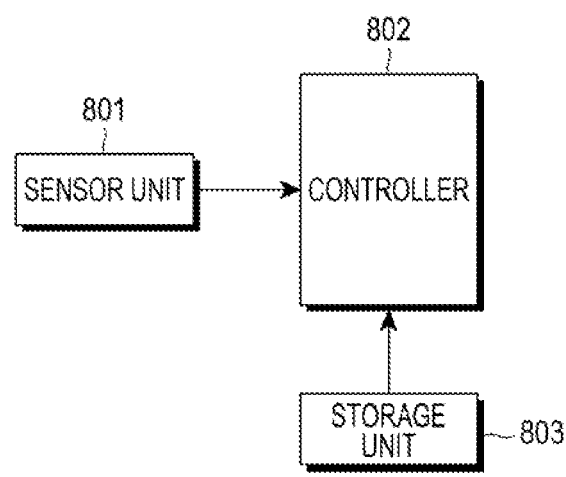
FIG. 8 illustrates an R-peak detection apparatus according to an embodiment of the present invention.

FIG. 8 illustrates an R-peak detection apparatus according to an embodiment of the present invention.

As illustrated in FIG. 8, the R-peak detection apparatus includes a sensor unit 801, a controller 802, and a storage unit 803.

The sensor unit 801 senses and receives the ECG signal from a living body. The sensor unit 801 may be implemented as an electronic device as described above, and it should be easily understood by those skilled in the art that the sensor unit 801 is not limited as long as the sensor unit 801 is capable of sensing the ECG signal. It should be easily understood by those skilled in the art that not only an element that can sense and receive the ECG signal such as the sensor unit 801 may be used, but also, the element may be replaced by an interface, which receives the ECG signal from an independent sensing means.

The controller 802 compares the input ECG signal with the ECG template that is read out from the storage unit 803, determines the similarity between the ECG signal and the ECG template, determines whether the similarity is equal to or greater than the threshold value, and determines an interval in which the similarity is greater than the threshold value as the R-peak. A configuration in which the controller 802 determines the similarity and determines the interval in which the similarity is equal to or greater than the threshold value as the R-peak has been described in detail, and thus, a further description thereof will be omitted. The controller 802 may be implemented in a form of a microprocessor, an Integrated Circuit (IC) chip, or a mini computer.

The storage unit 803 stores various programs, algorithms, or applications that are used for overall control of the R-peak detection apparatus, as well as the ECG signal template and the updated ECG signal template, which is generated during the updating process. Further, the storage unit 803 receives information about the threshold value. The storage unit 803 may be a volatile or non-volatile memory.

Figure 9:
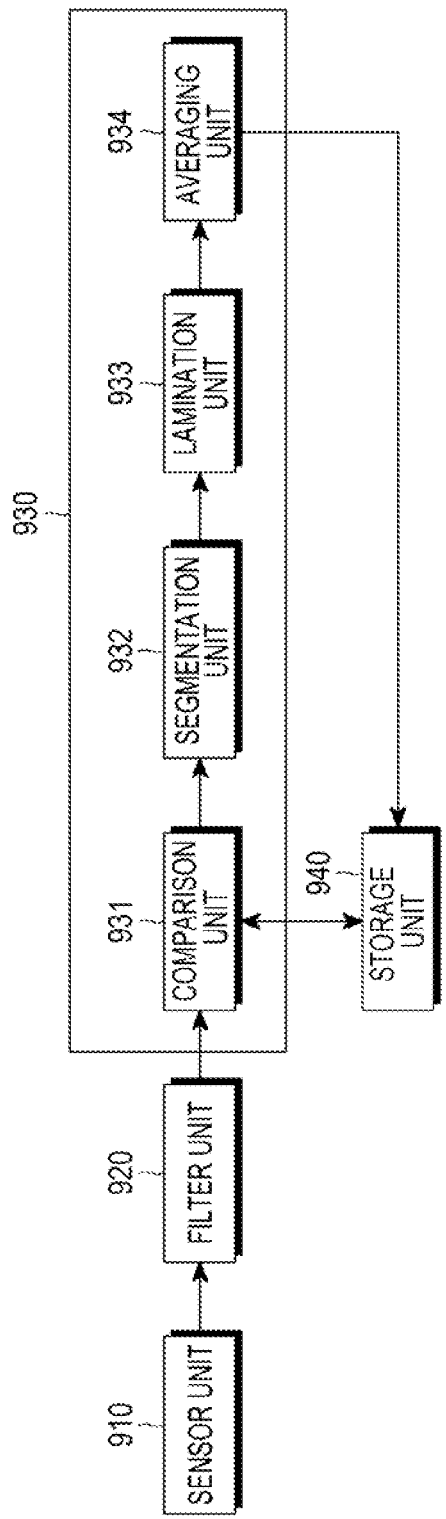
FIG. 9 illustrates an R-peak detection apparatus according to another embodiment of the present invention.

FIG. 9 illustrates an R-peak detection apparatus according to another embodiment of the present invention.

As illustrated in FIG. 9, the R-peak detection apparatus includes a sensor unit 910, a filter unit 920, a controller 930, and a storage unit 940. The controller 930 includes a comparison unit 931, a segmentation unit 932, a lamination unit 933, and an averaging unit 934.

The sensor unit 901 senses or receives the ECG signal.

The filter unit 920 filters the input ECG signal to remove noise therefrom. The filter unit 920 includes at least one of the high pass filter, the low pass filter, and the bypass filter. The filter unit 920 filters a frequency band corresponding to noise through various filters described above, alone or in combination thereof.

In order to determine the similarity between the ECG signal and the ECG template, the comparison unit 931 compares both signals, based on a correlation. Also, the comparison unit 931 determines the R-peak or the R-peak candidate based on the threshold value read out from the storage unit 940.

The segmentation unit 932 performs segmentation based on the R-peak candidate to generate at least one segment.

The lamination unit 933 laminates the at least one segment on one plane, and the averaging unit 934 averages the at least one segment laminated on the one plane to generate the updated ECG template.

The controller 930 repeats updating the ECG template, determines the similarity based on the updated ECG template, and updates the R-peak candidate by a preset number of times. When the controller 930 repeats the updating the ECG template, determining the similarity based on the updated ECG template, and updating the R-peak candidate by a preset number of times, the R-peak candidate may be determined as the R-peak.

Although not illustrated, the controller 930 may additionally include a comparison object determination unit for determining a part of the ECG signal as the comparison object interval. When the controller 930 includes the comparison object determination unit, the segmentation unit 932 performs segmentation on time serial data of the comparison object interval based on the R-peak candidate to generate at least one segment. The lamination unit 933 laminates the at least one segment and the averaging unit 934 averages the at least one laminated segment. The controller 930 may additionally include a propagation unit, which may propagate the averaged data in remaining intervals other than the comparison object interval to detect the R-peak.

While the present invention has been illustrated and described with reference to certain embodiments thereof, it will be understood by those skilled in the art that various changes in form and details may be made therein without departing from the spirit and scope of the present invention as defined by the appended claims and their equivalents.

What is claimed is:

1. A method of controlling of an R-peak detection apparatus which detects an R-peak from an ElectroCardioGram (ECG) signal, the method comprising:
   receiving the ECG signal;
   filtering the received ECG signal to remove noise from the ECG signal;
   reading out a pre-stored ECG template;
   comparing the received ECG signal with the pre-stored ECG template to determine a similarity between the ECG signal and the pre-stored ECG template;
   determining whether the similarity is equal to or greater than a threshold value; and
   when the similarity is equal to or greater than the threshold value, repeatedly updating the pre-stored ECG template according to a set number of times and determining a corresponding interval as the R-peak,
   wherein the threshold value is determined using an average and a distribution of a correlation between the ECG signal and the pre-stored ECG template.

2. The method of claim 1, wherein the similarity between the ECG signal and the pre-stored ECG template is determined based on a resulting value of a correlation between the ECG signal and the pre-stored ECG template.

3. The method of claim 2, wherein the resulting value of the correlation is determined by $$r_{xy} = \frac{\sum_{i=1}^{n}(x_i - \bar{x})(y_i - \bar{y})}{\sqrt{\sum_{i=1}^{n}(x_i - \bar{x})^2}\sqrt{\sum_{i=1}^{n}(y_i - \bar{y})^2}},$$

wherein $x_i$ denotes an i-th time serial data of an i-th ECG signal, $y_i$ is time serial data of an i-th ECG template, $\bar{x}$ denotes an average of the time serial data of the ECG signal, $\bar{y}$ is an average of the time serial data of the ECG template, $r_{xy}$ is the resulting value of the correlation, and n denotes a number of the time serial data.

4. The method of claim 1, further comprising, subsequent to determining the similarity and prior to determining the R-peak:
determining a corresponding interval in which the similarity is equal to or greater than the threshold value as an R-peak candidate;
processing the ECG signal based on the R-peak candidate to update the pre-stored ECG template;
determining an updated similarity by comparing the updated ECG template with the ECG signal; and
re-determining the R-peak candidate based on the updated similarity.

5. The method of claim 4, wherein re-determining the R-peak candidate comprises:
determining an interval in which the updated similarity is equal to or greater than the preset value as a new R-peak candidate.

6. The method of claim 4, wherein determining the updated similarity, and re-determining the R-peak candidate are performed the set number of times.

7. The method of claim 6, further comprising:
determining a current R-peak candidate as the R-peak, when updating the pre-stored ECG template, determining the updated similarity and re-determining the R-peak candidate are performed the set number of times.

8. The method of claim 4, wherein updating the pre-stored ECG template comprises:
performing segmentation on the time serial data of the ECG signal based on the R-peak to generate a plurality of segments;
laminating the plurality of segments; and
averaging the plurality of laminated segments to generate an updated ECG template.

9. The method of claim 4, wherein updating the pre-stored ECG template comprises:
determining a part of the ECG signal as a comparison object interval;
performing segmentation on time serial data of the comparison object interval based on the R-peak candidate to generate a plurality of segments;
laminating the plurality of segments;
averaging the plurality of laminated segments; and
propagating average data in remaining intervals other than the comparison object interval to determine the R-peak.

10. An R-peak detection apparatus for detecting an R-peak from an ElectroCardioGram (ECG) signal, the R-peak detection apparatus comprising:
a sensor unit which senses the ECG signal;
a filter unit which filters the ECG signal to remove noise therefrom;
a storage unit which stores an ECG template; and
a controller which compares the ECG signal with the ECG template to determine a similarity between the ECG signal and the ECG template, determines whether the similarity is equal to or greater than a threshold value, and when the similarity is equal to or greater than the threshold value, repeatedly updates the pre-stored ECG template according to a set number of times and determines a corresponding interval as the R-peak,
wherein the threshold value is determined using an average and a distribution of a correlation between the ECG signal and the ECG template.

11. The R-peak detection apparatus of claim 10, wherein the controller determines the similarity based on a resulting value of a correlation between the ECG signal and the ECG template.

12. The R-peak detection apparatus of claim 11, wherein the resulting value of the correlation is determined by $$r_{xy} = \frac{\sum_{i=1}^{n}(x_i - \bar{x})(y_i - \bar{y})}{\sqrt{\sum_{i=1}^{n}(x_i - \bar{x})^2}\sqrt{\sum_{i=1}^{n}(y_i - \bar{y})^2}},$$

wherein $x_i$ denotes an i-th time serial data of an i-th ECG signal, $y_i$ is time serial data of an i-th ECG template, $\bar{x}$ denotes an average of time serial data of the ECG signal, $\bar{y}$ is an average of time serial data of the ECG template, $r_{xy}$ is the resulting value of the correlation, and n denotes a number of the time serial data.

13. The R-peak detection apparatus of claim 10, wherein the controller determines a corresponding interval in which the similarity is equal to or greater than the threshold value as an R-peak candidate, processes the ECG signal based on the R-peak candidate to update the ECG template, determines an updated similarity by comparing the updated ECG template with the ECG signal, and re-determines the R-peak candidate based on the updated similarity.

14. The R-peak detection apparatus of claim 13, wherein the controller re-determines the R-peak candidate by determining an interval in which the updated similarity is equal to or greater than the threshold value as a new R-peak candidate and storing the new R-peak candidate.

15. The R-peak detection apparatus of claim 13, wherein the controller repeatedly determines the updated similarity, and re-determines the R-peak candidate the set number of times.

16. The R-peak detection apparatus of claim 15, wherein the controller determines a current R-peak candidate as the R-peak, when the controller updates the ECG template, determines the updated similarity, and re-determines the R-peak candidate are repeated the set number of times.

17. The R-peak detection apparatus of claim 13, wherein the controller comprises:
a segment unit which performs segmentation on the time serial data of the ECG signal based on the R-peak candidate to generate a plurality of segments;
a lamination unit which laminates the plurality of segments; and
an averaging unit which averages the plurality of laminated segments to generate an updated ECG template.

18. The R-peak detection apparatus of claim 13, wherein the controller comprises:
- a comparison object determination unit which determines a part of the ECG signal as a comparison object interval;
- a segmentation unit which performs segmentation on time serial data of the comparison object interval based on the R-peak candidate to generate a plurality of segments;
- a lamination unit which laminates the plurality of segments;
- an averaging unit which averages the plurality of laminated segments; and
- a propagation unit which propagates average data in remaining intervals other than the comparison object interval to determine the R-peak.

* * * * *